(12) United States Patent
Nelson et al.

(10) Patent No.: US 9,267,926 B2
(45) Date of Patent: Feb. 23, 2016

(54) SELF ADJUSTING CORNER SCANNER

(71) Applicant: Spirit AeroSystems, Inc., Wichita, KS (US)

(72) Inventors: W. Robert Nelson, Wichita, KS (US); Adam Joseph Donar, Wichita, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 540 days.

(21) Appl. No.: 13/674,647

(22) Filed: Nov. 12, 2012

(65) Prior Publication Data

US 2014/0130617 A1  May 15, 2014

(51) Int. Cl.
*G01N 29/265* (2006.01)
*G01B 17/06* (2006.01)
*G01B 5/213* (2006.01)
*G01B 21/20* (2006.01)

(52) U.S. Cl.
CPC .............. *G01N 29/265* (2013.01); *G01B 5/213* (2013.01); *G01B 17/06* (2013.01); *G01B 21/20* (2013.01)

(58) Field of Classification Search
CPC ...... G01B 5/0009; G01B 5/213; G01B 17/06; G01B 21/20; G01N 29/265
USPC ........... 73/583, 620, 628–629, 634, 640–641, 73/865.8
See application file for complete search history.

(56) References Cited

U.S. PATENT DOCUMENTS 3,541,840 A * 11/1970 Phelan .......................... 73/641 X
5,050,128 A *  9/1991 Saitoh et al. ..................... 367/7

FOREIGN PATENT DOCUMENTS

| DE | 2360780 B  | * |  2/1975 | ............. G01B 5/213 |
| EP | 1600729 A2 | * | 11/2005 | ............. G01B 5/213 |
| EP | 2345881 A1 | * |  7/2011 | ............. G01B 21/20 |
| SU |  395764 A  | * |  1/1974 | |

* cited by examiner

*Primary Examiner* — Paul West
(74) *Attorney, Agent, or Firm* — Hovey Williams LLP

(57) ABSTRACT

An apparatus for inspecting a curved portion of a manufactured part comprises a frame, a sensor, a plunger, and a linking mechanism. The frame may include a first contact wall and an opposing second contact wall. Each contact wall may contact a planar portion of the part adjacent to the curved portion and may be oriented at an angle corresponding to an angle of the planar portions of the part adjacent to the curved portion. The sensor may transmit at least one signal to and receive at least one signal from the part. The plunger may contact the surface of the part and move as a radius of curvature of the part changes. The linking mechanism may couple to the plunger and may adjust the height of the sensor above a surface of the part in response to motion of the plunger.

21 Claims, 7 Drawing Sheets

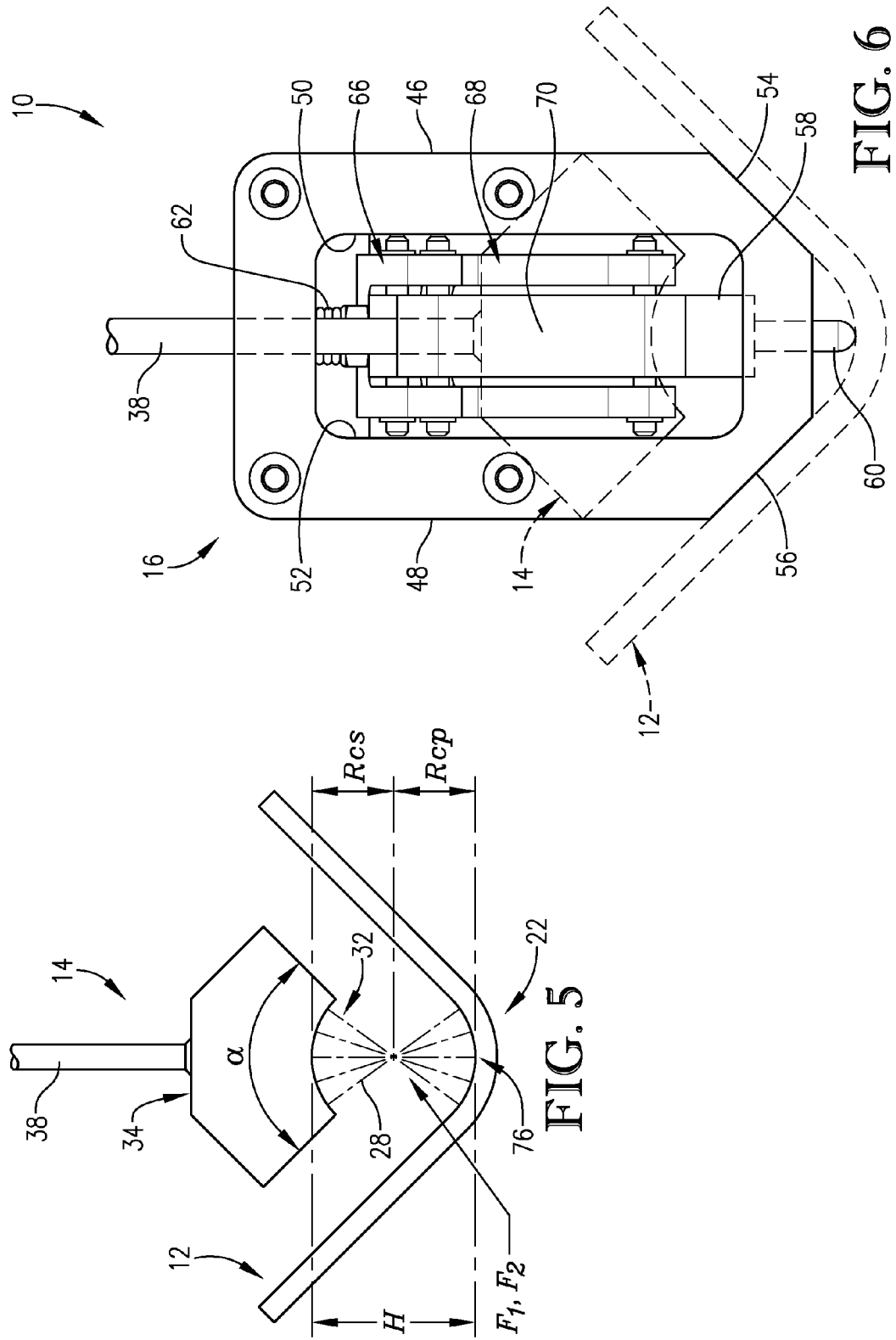

SELF ADJUSTING CORNER SCANNER

BACKGROUND OF THE INVENTION

1. Field of the Invention

Embodiments of the current invention relate to non-destructive inspection of manufactured parts. More particularly, embodiments of the current invention relate to apparatuses to inspect a curved portion of a manufactured part.

2. Description of the Related Art

Non-destructive inspection involves the examination of parts, often in a production environment, wherein some characteristic of the part is measured to evaluate a certain aspect of the part, such as the quality of construction. As opposed to other techniques to gauge the quality of a part or to find defects, such as cross sectioning, drilling or excising a portion of the part, all of which may destroy the part or at least render the part unusable, non-destructive inspection does not typically harm the part in any way. Often, the methods of non-destructive inspection include scanning a part by transmitting a form of energy, such as ultrasonic waves, at the part and recording the reflected or perhaps refracted energy to form an image or profile of the part. Typically, the scan is performed by rastering or otherwise sweeping a transmitting and receiving sensor or an array of sensors over the surface of the part at a fixed height.

Some parts, such as aircraft components like fuselage frames, shear ties, wing spars, and others, include two or more planar portions that form a "C", "V", or "L" shaped bend with a smooth curve therebetween. The radius of curvature of the bend may change from part to part or even within the same part. The shape of the sensor array may be adapted to inspect the curvature, and the sensor array may be swept across the curvature at a certain height in order to perform the inspection. However, maintaining the correct height above the curvature when the radius of curvature changes may be difficult.

SUMMARY OF THE INVENTION

Embodiments of the current invention solve the above-mentioned problems and provide a distinct advance in the art of non-destructive inspection. More particularly, embodiments of the invention provide apparatuses that automatically adjust the height of a non-destructive inspection sensor.

Various embodiments of the current invention provide an apparatus for inspecting a curved portion of a manufactured part. The apparatus broadly comprises a frame, a sensor, a plunger, and a linking mechanism. The frame may include a first contact wall and an opposing second contact wall. Each contact wall may contact a planar portion of the part adjacent to the curved portion and may be oriented at an angle corresponding to an angle between the planar portions of the part adjacent to the curved portion. The sensor may include a plurality of sensing elements that are positioned on a concave arcuate surface. Each sensing element may transmit and receive a signal. The plunger may contact the surface of the part and move as a radius of curvature of the part changes. The linking mechanism may couple to the frame and the plunger and may adjust the height of the sensor above a surface of the part in response to motion of the plunger, wherein the height corresponds to a sum of a radius of curvature of the concave arcuate surface and the radius of curvature of the curved portion.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein:

FIG. 5 is a rear view of a sensor of the apparatus shown in isolation transmitting and receiving signals from the female surface of the part;

FIG. 6 is a rear view of the apparatus inspecting the female corner of the part;

Figure 1:
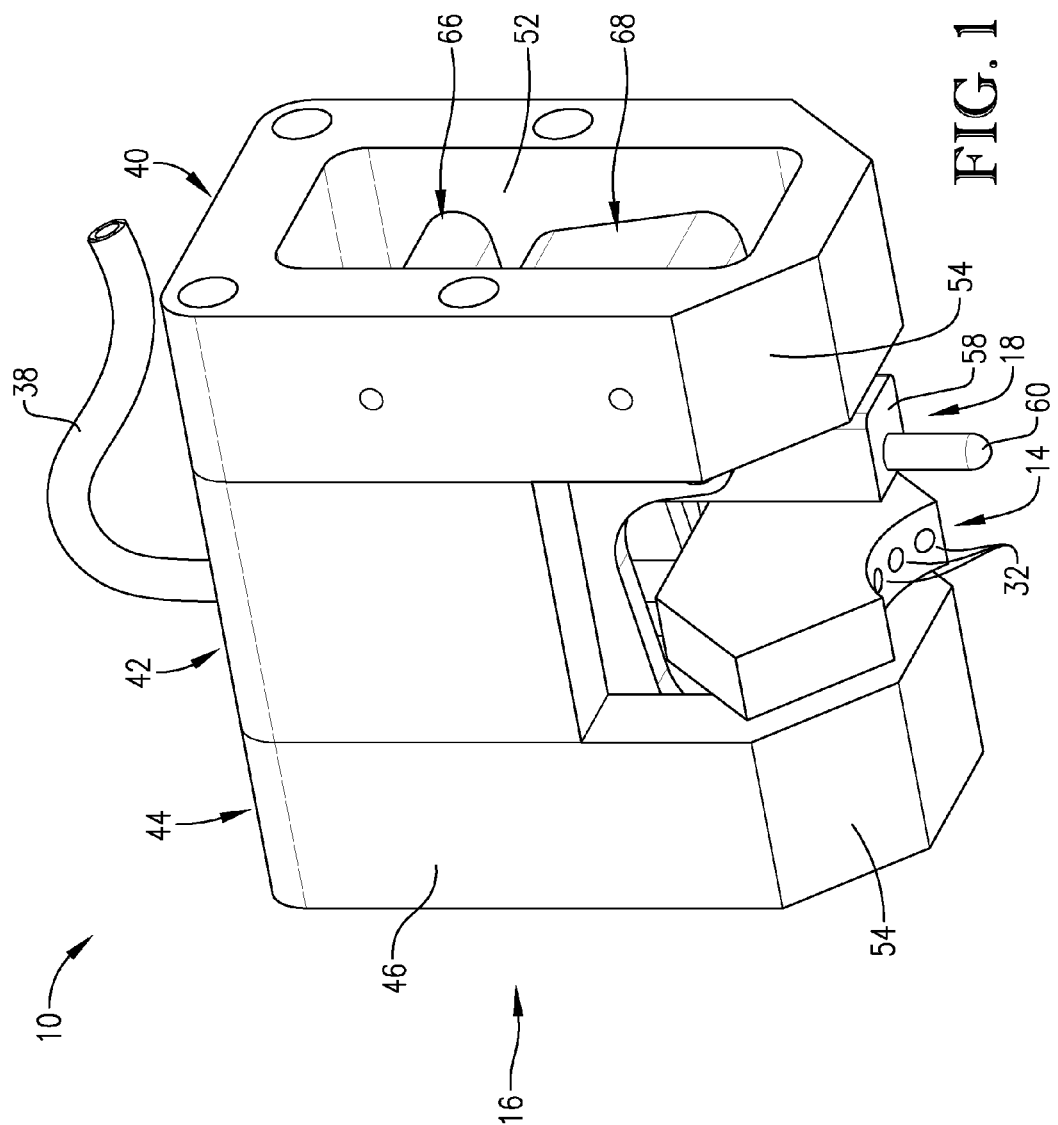
FIG. 1 is a front, lower perspective view of an apparatus, constructed in accordance with various embodiments of the current invention, that automatically adjusts the height of a non-destructive inspection sensor.
Figure 2:
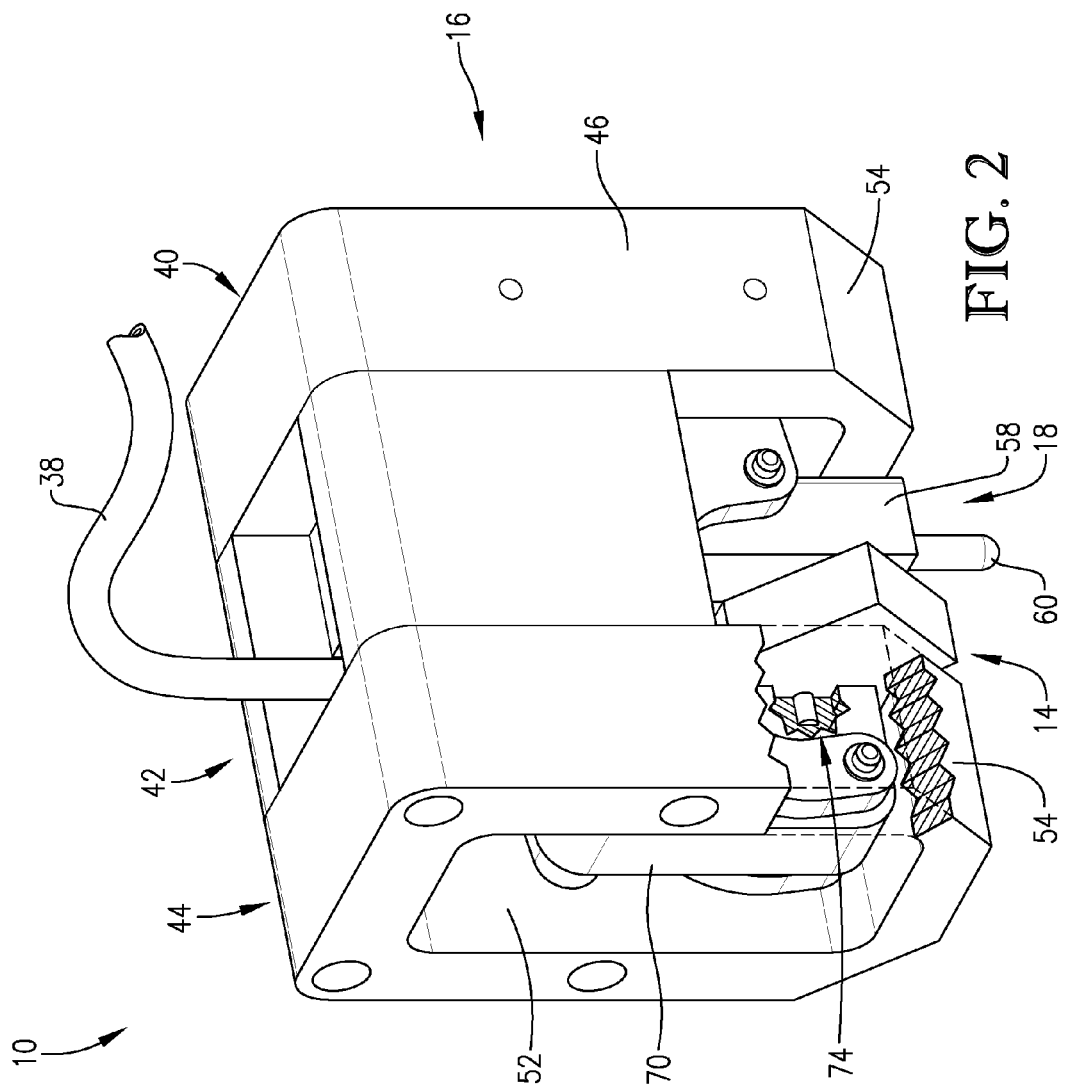
FIG. 2 is a rear, upper perspective view of the apparatus with a portion of a frame cut away revealing the connection of a sensor to a sensor block.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Figure 3:
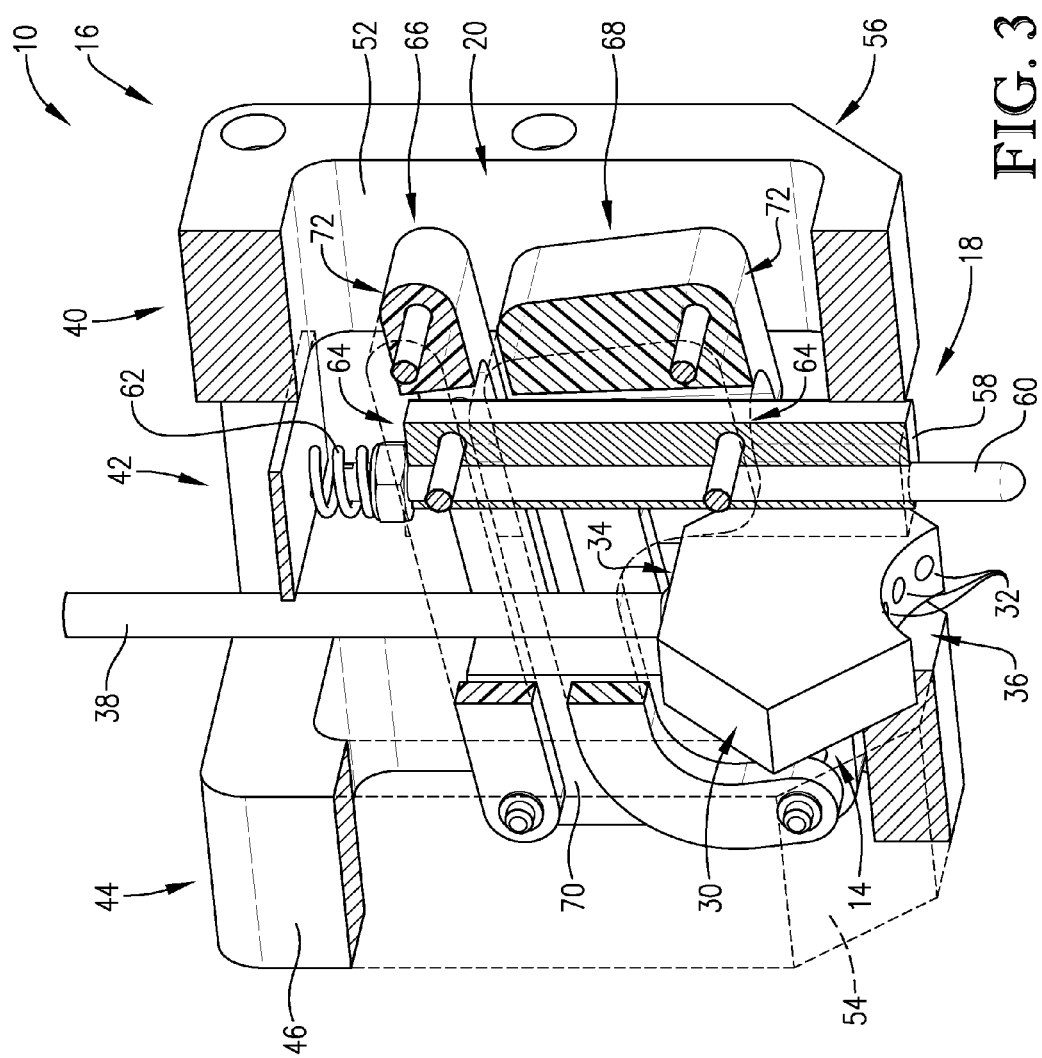
FIG. 3 is a front, lower perspective view of the apparatus with a portion of the frame, a linking mechanism, and a plunger cut away.
Figure 4:
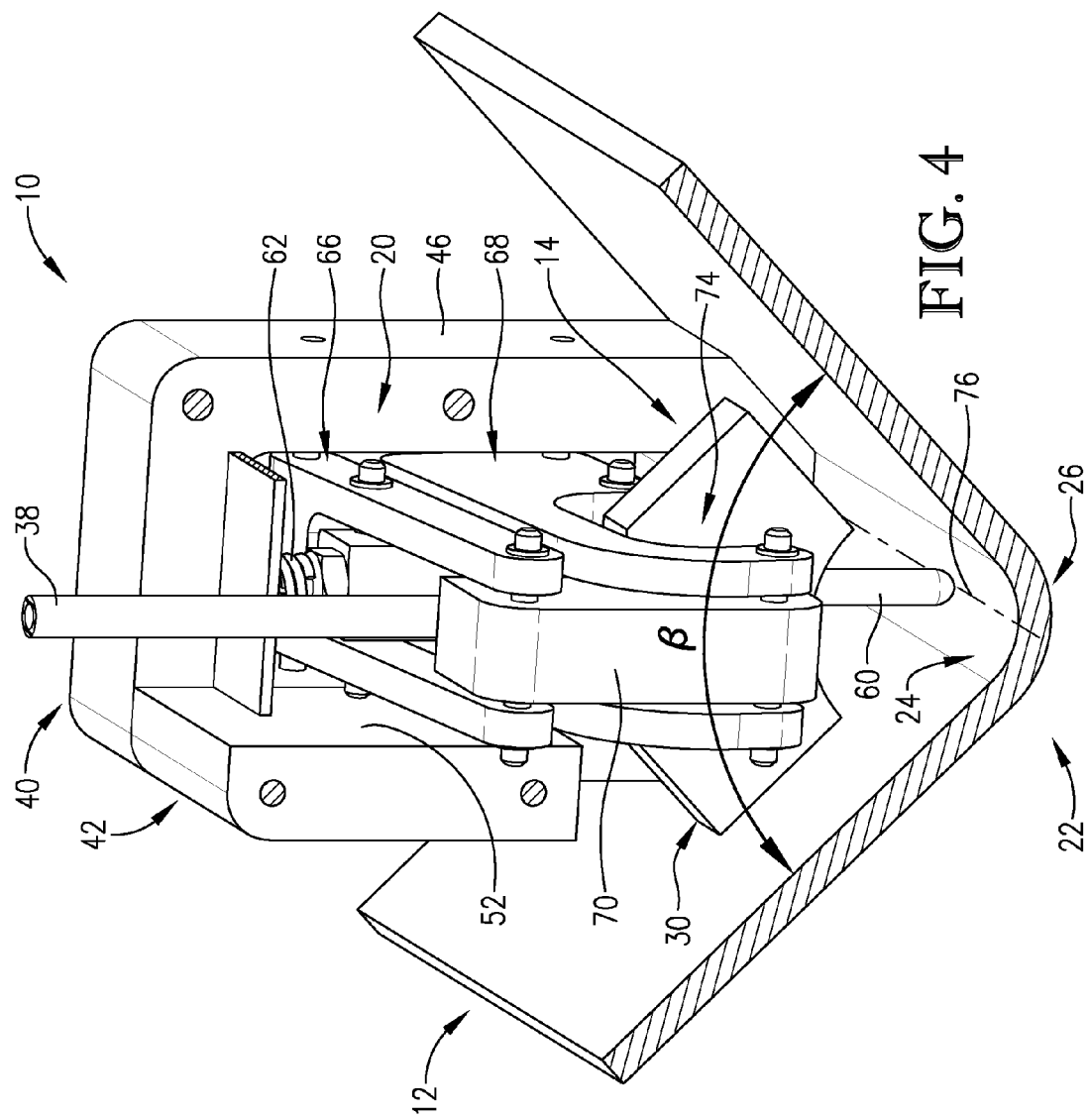
FIG. 4 is a rear, upper perspective view of the apparatus inspecting a female corner of a part with a portion of the frame cut away.

An apparatus 10 for inspecting a curved portion of a manufactured part 12, constructed in accordance with a first embodiment of the current invention, is shown in FIGS. 1-4 and 6. The apparatus 10 may broadly comprise a sensor 14, a frame 16, a plunger 18, and a linking mechanism 20. The part 12 may be an aircraft component, such as a fuselage frame, a shear tie, a wing spar, or the like. The part 12, as shown in FIGS. 4-6, may have a "C", "V", or "L" shaped bend between two or more planar portions such as a web or a flange with a corner 22 located therebetween. Generally, the corner 22 has a regular, smooth curvature, such as an arc that forms a portion of the circumference of a circle. In addition, the corner 22 has a female side 24 along internal surfaces of the part 12 and a male side 26 along external surfaces.

Throughout this description, directional terms, such as left, right, forward, rear, upper, lower, and the like, may be used to refer to components and aspects of the current invention as they appear in the figures. However, the current invention is not limited to function only in the orientations shown in the figures and may function in nearly any orientation. It is noted that in other orientations, the terms still apply in a relative sense.

The sensor 14 generally transmits a signal 28 to the part 12 and receives the signal 28 that is reflected back. The sensor 14 may utilize optical, ultrasonic, or electromagnetic signals to inspect the part. The sensor 14 may include a housing 30 and a plurality of sensing elements 32 that form an array. The housing 30 may include four sidewalls with a top wall 34 and a bottom wall 36. Each sensing element 32 may include a transducer that both transmits and receives signals or a transmitter to transmit signals and a separate receiver to receive signals that are positioned adjacent one another. The sensor 14 may further include a cable 38 to communicate data to and from the sensing elements 32.

The sensor 14 is shown in isolation with a part 12 in FIG. 5. Each sensing element 32 may transmit the signal 28 to the part 12 and receive the signal 28 that is reflected from the surface of the part 12 at a normal or near-normal angle. In order to properly reflect signals 28 along the corner 22, the sensing elements 32 may be arranged in a concave, arcuate shape along the bottom wall of the housing 30. The angle α of the array of sensing elements 32 on the bottom wall of the housing 30 seen in FIG. 5 is generally the same as the angle β between planar portions of the part 12 seen in FIG. 4. The number of sensing elements 32 that are implemented in the housing 30 may depend on the desired resolution of scanning the part 12 and the amount of space available along the bottom wall of the housing 30. For example, greater scanning resolution generally requires a greater number of sensing elements 32. But, a greater number of sensing elements 32 requires more space along the bottom wall of the housing 30.

Referring to FIG. 5, the array of sensing elements 32 has a center of curvature that is also a point at which the signals 28 transmitted from the sensing elements 32 intersect one another or a first focus F1. The distance from the focus F1 to any of the sensing elements 32 is a radius of curvature Rcs for the sensor 14. In addition, the corner 22 of the part 12 has a center of curvature that is also a point at which the signals 28 reflected from the surface of the corner 22 intersect one another or a second focus F2. The distance from the focus F2 to any point of the corner 22 is a radius of curvature Rcp for the part 12. In order for the transmitted signals 28 to be properly reflected from the corner 22 of the part 12, the sensor 14 must be positioned at a height H above the corner 22 where the focus F1 of the sensor 14 coincides with the focus F2 of the corner 22. Accordingly, the height H is equal to the sum of the radius of curvature Rcs of the sensor 14 and the radius of curvature Rcp of the part 12. Since the radius of curvature Rcs for the sensor 14 is typically fixed, the height H of the sensor 14 above the corner 22 is determined by the radius of curvature Rcp of the part 12. Therefore, the other components of the current invention function to keep the sensor 14 at the proper height H as the radius of curvature Rcp of the part 12 changes.

The frame 16 generally contacts the surface of the part 12 during scanning and retains the linking mechanism 20. The frame 16 may have a hollow interior and may include a forward section 40, a central section 42, and a rear section 44. The frame 16 may also include a left sidewall 46 and a right sidewall 48 located on opposing lengthwise sides. The forward section 40 and the rear section 44 may each include a left internal wall 50 and a right internal wall 52. The left and right internal walls 50, 52 of the forward section 40 may retain the linking mechanism 20. The forward section 40 and the rear section 44 may also each include a left contact wall 54 and a right contact wall 56 located at the lower edge of the left sidewall 46 and the right sidewall 48, respectively. The left and right contact walls 54, 56 generally contact or slide along the surface of the part 12 during scanning. The left contact wall 54 and the right contact wall 56 may each be tapered inward and downward at an angle from the left and right sidewalls 46, 48. The angle of taper may correspond to or be equal to the angle β between planar portions of the part 12, as seen in FIG. 4. The forward section 40 and the rear section 44 may be manufactured from low friction material or the left and right contact walls 54, 56 may have a low friction coating in order to reduce the friction between the frame 16 and the part 12 during scanning.

The plunger 18 generally senses the radius of curvature Rcp of the part 12 by contacting the surface of the corner 22 and may move in response to changes in the radius of curvature Rcp. The plunger 18 may include a body 58, a stem 60, and a biasing element 62. The body 58 may be generally elongated with four sidewalls and may rotatably couple to linking mechanism 20 along opposing sidewalls. The point at which the body 58 couples to the linking mechanism 20 may be considered a plunger attachment point 64, as seen in FIG. 3. The stem 60 may be rodlike or cylindrical and may couple to and extend from the lower end of the body 58. The stem 60 may include a rounded tip so as not to scratch the surface of the part 12 while it is in contact with the corner 22. The stem 60 may also be threaded where it couples to the body 58 in order to adjust the amount of extension of the stem 60 from the body 58. The biasing element 62 generally presses downward on the plunger 18 such that the stem 60 is urged to remain in contact with the corner 22. The biasing element 62 may include a spring or similar device that couples to the frame 16 and applies a downward force on the body 58.

The linking mechanism 20 positions the sensor 14 at the proper height H above the surface of the corner 22 of the part 12. Generally, the linking mechanism 20 may include any combination of mechanical components or a mechanical assembly that maintains the position of the sensor 14 relative to the plunger 18. Furthermore, the linking mechanism 20 may include any combination of mechanical components or a mechanical assembly that translates the motion of the plunger 18 to motion of the sensor 14.

In various embodiments, the linking mechanism 20 may be located between the left and right internal walls 50, 52 of the frame 16 and may include an upper link 66, a lower link 68, and a sensor block 70. The upper link 66 and the lower link 68 may be elongated and each may include a forward portion, a central portion, and a rear portion that correspond to similarly-named sections of the frame 16. The forward portion of the upper link 66 and the lower link 68 may be rotatably coupled to the left and right internal walls 50, 52 of the forward section 40 such that the rear end of the upper and lower links 66, 68 is operable to move in the vertical direction. The point at which the linking mechanism 20 couples to the forward section 40 may be considered a linking mechanism pivot point 72, as seen in FIG. 3. The central portion of the upper and lower links 66, 68 may be rotatably coupled to the plunger 18. The rear portion of the upper and lower links 66, 68 may be rotatably coupled to the sensor block 70 such that the sensor block 70 moves in the vertical direction with the upper and lower links 66, 68 but the sensor block 70 maintains an upright or surface normal orientation while it moves vertically. The point at which the linking mechanism 20 couples to the sensor block 70 may be considered a sensor attachment point 74, as seen in FIG. 4. The sensor block 70 may be generally box shaped with a forward wall to which the sensor 14 is attached. Thus, the sensor 14 may move in the vertical direction with the sensor block 70 while maintaining its surface normal orientation. In various embodiments, the sensor 14 may include the sensor block 70. In some embodiments, the sensor 14 may directly couple to the rear end of the linking mechanism 20.

The apparatus 10 may function as follows. During a scan, the apparatus 10 may be moved while the part 12 is held stationary, the part 12 may be moved while the apparatus 10 is held stationary, or both the part 12 and the apparatus 10 may be moved at the same time. Either the apparatus 10 or the part 12 may be moved by automated machinery.

The sensor 14 may be connected to electronic equipment that can send and receive signals to and from the sensing elements 32. The apparatus 10 may be positioned on the part 12 such that the left and right contact walls 54, 56 contact the planar portions of the part 12 that are adjacent to the corner 22. The stem 60 of the plunger 18, as urged by the biasing element 62, should contact the surface of the corner 22. The sensing elements 32 may transmit and receive signals 28 to and from the surface of the corner 22 of the part 12. During the scanning process, the apparatus 10 may be moved relative to the part 12 as the sensing elements 32 continue to transmit and receive signals 28 in order to inspect the corner 22 of the part 12.

The linking mechanism 20 may adjust the height H of the sensor 14 according to the radius of curvature Rcp of the corner 22 of the part 12. The corner 22 generally has a center 76 which is the point that is contacted by the stem 60 during the scanning process. The center 76 of the corner 22 moves up and down relative to the frame 16 as the radius of curvature Rcp of the part 12 changes. The center 76 generally moves up for an increasing radius of curvature Rcp and down for a decreasing radius of curvature Rcp. As the center 76 moves up and down, so does the stem 60 and, in turn, the plunger 18. Vertical motion of the plunger 18 creates vertical motion of the sensor 14 through the linking mechanism 20.

Figure 7:
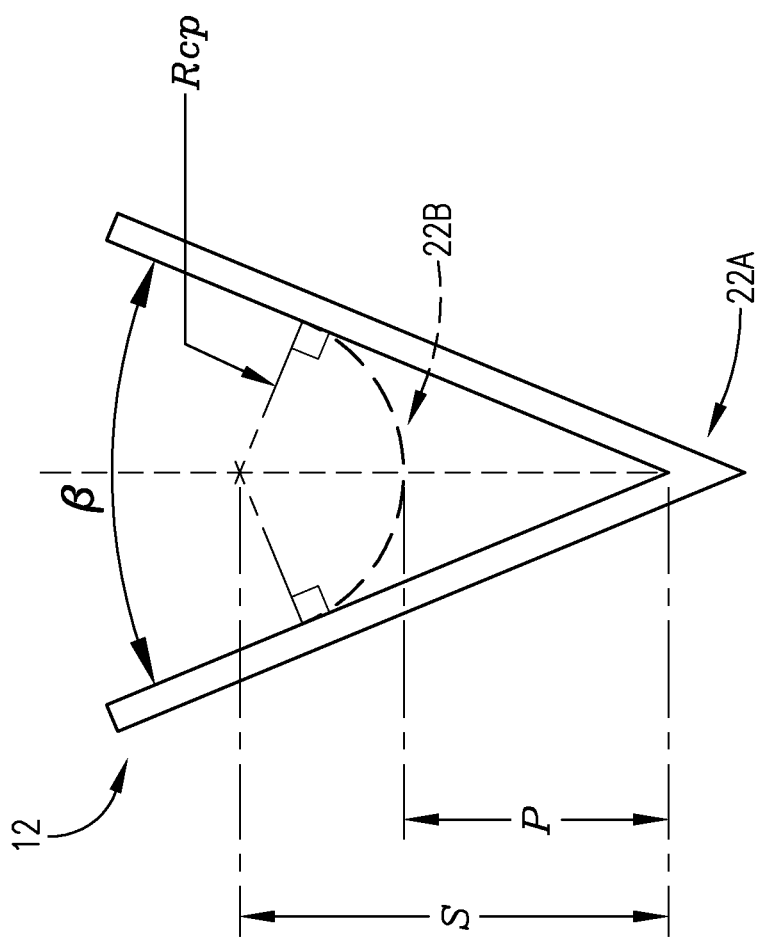
FIG. 7 is a side view of the part with a varying radius of curvature.

Generally, the vertical motion of the plunger 18 for a given change in the radius of curvature Rcp depends on the angle β between planar portions of the part 12. Referring to FIG. 7, a vertical distance P that the plunger 18 travels for a change in radius of curvature Rcp is shown for a first corner 22A with a radius of curvature Rcp of zero and a second corner 22B with a radius of curvature Rcp greater than zero. A distance S that the sensor 14 travels is shown as well. It can be derived from the drawing that P=S−Rcp. Distance S is related to the angle β and Rcp through the following: S=Rcp/sin(β/2). Substitution for S yields: P=Rcp/sin(β/2)−Rcp.

On the linking mechanism 20, the distances from the sensor attachment point 74 to the linking mechanism pivot point 72 and the plunger attachment point 64 to the linking mechanism pivot point 72 are proportional to the distances S and P, respectively. The ratio of the distance between the sensor attachment point 74 and the linking mechanism pivot point 72 to the distance between the plunger attachment point 64 and the linking mechanism pivot point 72 is proportional to S/P, which equals:

$$\frac{\frac{Rcp}{\sin(\beta/2)}}{\frac{Rcp}{\sin(\beta/2)} - Rcp}$$

Reducing terms yields: $1/[1-\sin(\beta/2)]$. Thus, the linking mechanism 20 may be constructed with the distance from the sensor attachment point 74 to the linking mechanism pivot point 72 being the distance from the plunger attachment point 64 to the linking mechanism pivot point 72 times $1/[1-\sin(\beta/2)]$.

With the apparatus 10 of the current invention, non-destructive inspection of a part 12 with a curved corner 22 may be performed for corners 22 with variable radii of curvature—even if the radius of curvature changes within the same corner 22. Furthermore, since the biasing element 62 of the plunger 18 urges the stem 60 to maintain contact with the surface of the part 12, the apparatus 10 may be utilized in any orientation.

Figure 8:
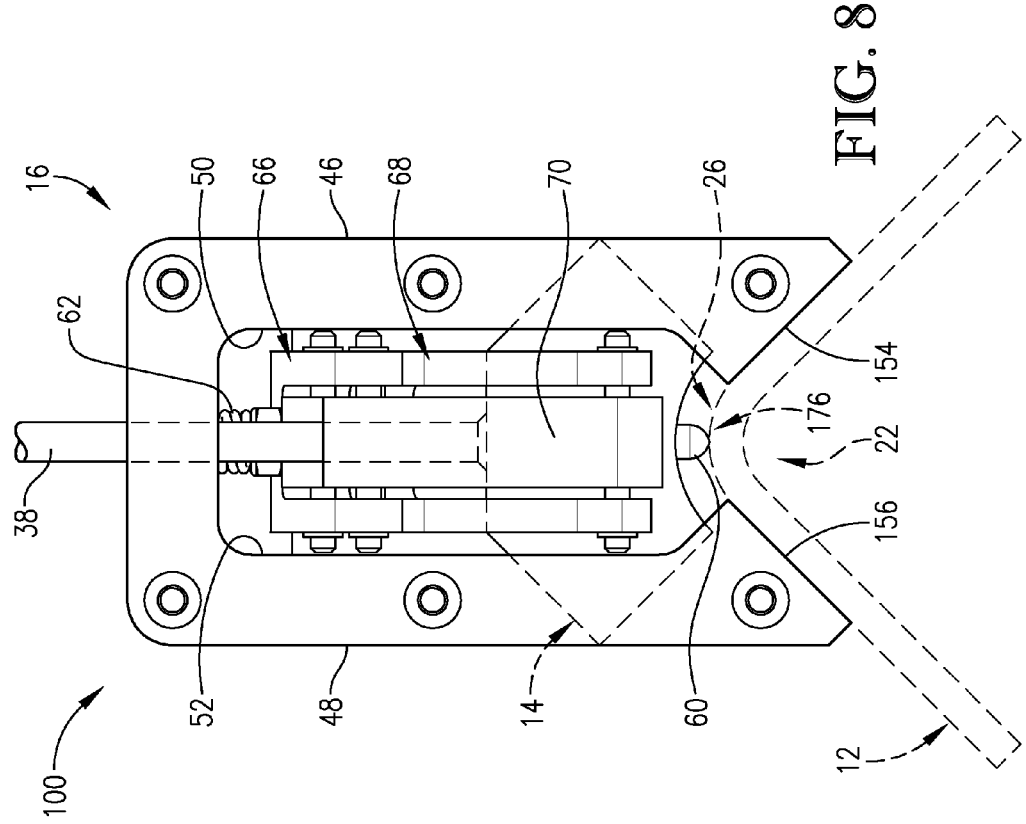
FIG. 8 is a rear view of an apparatus, constructed in accordance with a second embodiment of the current invention, inspecting a male corner of the part.

An apparatus 100, constructed in accordance with a second embodiment of the current invention, is shown in FIG. 8. The apparatus 100 may be substantially similar to the apparatus 10 in function and structure with the following exception. The apparatus 100 may include a left contact wall 154 and a right contact wall 156 located at the lower edge of the left sidewall 46 and the right sidewall 48, respectively. Whereas the left contact wall 54 and the right contact wall 56 are each tapered inward and downward at an angle from the left and right sidewalls 46, 48, the left contact wall 154 and the right contact wall 156 may be tapered inward and upward. Given this structure, the left and right contact walls 154, 156 may contact the outer surfaces of the planar portions of the part 12 to inspect the male side 26 of the corner 22.

Figure 9:
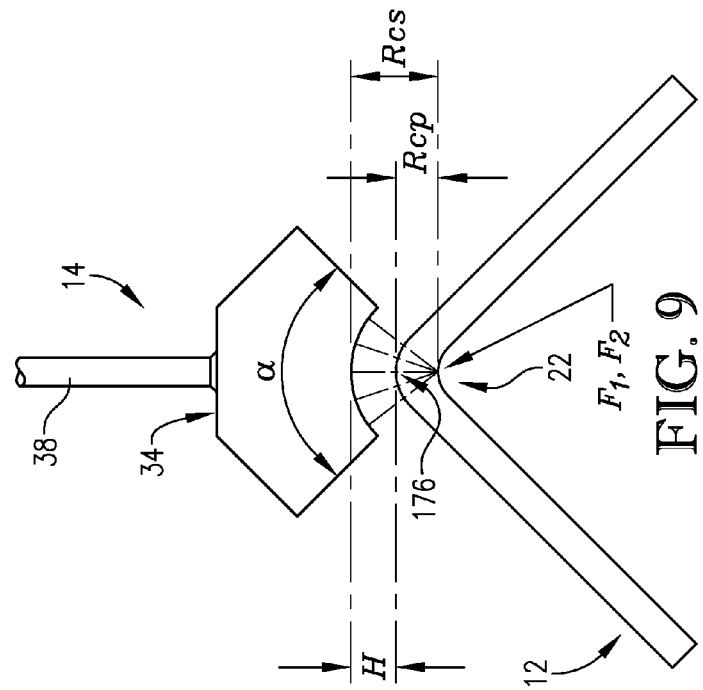
FIG. 9 is a rear view of a sensor of the apparatus of FIG. 8 shown in isolation transmitting and receiving signals from a male surface of the part.

The center of curvature of the male side 26 of the corner 22 is inward toward the inner surface of the part 12. In order for the focus F1 of the sensor 14 to coincide with the focus F2 of the corner 22, the outer surface of the corner 22 is positioned within the radius of curvature Rcs of the sensor 14, as can be seen in FIG. 9. Thus, the height H of the sensor 14 above the outer surface of the corner 22 is equal to the radius of curvature Rcs of the sensor 14 minus the radius of curvature Rcp of the part 12.

The operation of the apparatus 100 is substantially similar to that of the apparatus 10. The apparatus 100 may be positioned on the part 12 such that the left and right contact walls 154, 156 contact the outer surface of the part 12 adjacent to the male side 26 of the corner 22. The sensing elements 32 may transmit and receive signals 28 to and from the surface of the corner 22 of the part 12. And, the apparatus 100 may be moved relative to the part 12 as the sensing elements 32 continue to transmit and receive signals 28 in order to inspect the male side 26 of the corner 22 of the part 12.

The linking mechanism 20 may adjust the height H of the sensor 14 according to the radius of curvature Rcp of the corner 22 of the part 12. The male side 26 of the corner 22 has a center 176 as well, which is the point that is contacted by the stem 60 during the scanning process. Like the female side 24 of the corner 22, the center 176 of the corner 22 moves up and down relative to the frame 16 as the radius of curvature Rcp of the part 12 changes. In contrast to the female side 24, the center 76 generally moves down for an increasing radius of curvature Rcp and up for a decreasing radius of curvature Rcp. The linking mechanism 20 adjusts the height of the sensor 14 in the same fashion as described above for the changes in the radius of curvature Rcp of the part 12.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An apparatus for inspecting a curved portion of a manufactured part, the apparatus comprising:
    a sensor configured to transmit at least one signal to and receive at least one signal from the part;
    a plunger configured to contact a surface of the part and move normal to the surface relative to a change in a radius of curvature of the curved portion of the part; and
    a linking mechanism connecting the sensor to the plunger, the linking mechanism receiving motion from the plunger and supplying motion to the sensor in order to adjust a distance of the sensor from a surface of the part in response to relative motion of the plunger.

2. The apparatus of claim 1, further comprising a frame retaining the linking mechanism and including a first contact wall and an opposing second contact wall, each contact wall configured to contact a planar portion of the part adjacent to the curved portion.

3. The apparatus of claim 2, wherein the first and second contact walls are each oriented at an angle corresponding to an angle between the planar portions of the part adjacent to the curved portion.

4. The apparatus of claim 2, further comprising a plunger biasing element coupled to the frame and one end of the plunger and configured to urge the plunger to contact the surface of the part.

5. The apparatus of claim 2, wherein the linking mechanism is rotatably coupled to the frame at a linking mechanism pivot point, rotatably coupled to the sensor at a sensor attachment point, and rotatably coupled to the plunger at a plunger attachment point, wherein a distance between the sensor attachment point and the linking mechanism pivot point is equal to a distance between the plunger attachment point and the linking mechanism pivot point times the relationship: $1/[1-\sin(\beta/2)]$, wherein $\beta$ is an angle between planar portions of the part adjacent to the curved portion.

6. The apparatus of claim 2, wherein the linking mechanism includes an upper link and a lower link, each rotatably coupled to the frame, the plunger, and a sensor block such that the relative orientation of the sensor block is maintained when the plunger moves.

7. The apparatus of claim 1, wherein the sensor includes a plurality of sensing elements that are positioned on a concave arcuate surface.

8. The apparatus of claim 7, wherein the sensing elements are ultrasonic transducers.

9. The apparatus of claim 7, wherein the distance of the sensor from the curved portion of the part corresponds to a sum of a radius of curvature of the concave arcuate surface and the radius of curvature of the curved portion.

10. An apparatus for inspecting a curved portion of a manufactured part, the apparatus comprising:
    a frame including a first contact wall and an opposing second contact wall, each contact wall configured to contact a planar portion of the part adjacent to the curved portion and oriented at an angle corresponding to an angle between the planar portions of the part adjacent to the curved portion;
    a sensor configured to transmit at least one signal to and receive at least one signal from the part;
    a plunger configured to contact a surface of the part and move normal to the surface relative to a change in a radius of curvature of the curved portion of the part; and
    a linking mechanism coupled to the frame and the plunger and configured to adjust a distance of the sensor from a surface of the part in response to relative motion of the plunger.

11. The apparatus of claim 10, further comprising a plunger biasing element coupled to the frame and one end of the plunger and configured to urge the plunger to contact the surface of the part.

12. The apparatus of claim 10, wherein the sensor includes a plurality of sensing elements that are positioned on a concave arcuate surface.

13. The apparatus of claim 12, wherein the sensing elements are ultrasonic transducers.

14. The apparatus of claim 12, wherein the distance of the sensor from the curved portion of the part corresponds to a sum of a radius of curvature of the concave arcuate surface and the radius of curvature of the curved portion.

15. The apparatus of claim 10, wherein the linking mechanism is rotatably coupled to the frame at a linking mechanism pivot point, rotatably coupled to the sensor at a sensor attachment point, and rotatably coupled to the plunger at a plunger attachment point, wherein a distance between the sensor attachment point and the linking mechanism pivot point is equal to a distance between the plunger attachment point and the linking mechanism pivot point times the relationship: $1/[1-\sin(\beta/2)]$, wherein $\beta$ is an angle between planar portions of the part adjacent to the curved portion.

16. The apparatus of claim 10, wherein the linking mechanism includes an upper link and a lower link, each rotatably coupled to the frame, the plunger, and a sensor block such that the relative orientation of the sensor block is maintained when the plunger moves.

17. An apparatus for inspecting a curved portion of a manufactured part, the apparatus comprising:
    a frame including a first contact wall and an opposing second contact wall, each contact wall configured to contact a planar portion of the part adjacent to the curved portion and oriented at an angle corresponding to an angle between the planar portions of the part adjacent to the curved portion;
    a plurality of sensing elements that are positioned on a concave arcuate surface, each sensing element configured to transmit and receive a signal;
    a plunger configured to contact a surface of the part and move normal to the surface relative to a change in a radius of curvature of the curved portion of the part; and
    a linking mechanism coupled to the frame and the plunger and configured to adjust a distance of the sensing elements from a surface of the part in response to relative motion of the plunger, the distance corresponding to a sum of a radius of curvature of the concave arcuate surface and the radius of curvature of the curved portion.

18. The apparatus of claim 17, further comprising a plunger biasing element coupled to the frame and one end of the plunger and configured to urge the plunger to contact the surface of the part.

19. The apparatus of claim 17, wherein the linking mechanism is rotatably coupled to the frame at a linking mechanism pivot point, rotatably coupled to the sensing elements at a sensor attachment point, and rotatably coupled to the plunger at a plunger attachment point, wherein a distance between the sensor attachment point and the linking mechanism pivot point is equal to a distance between the plunger attachment point and the linking mechanism pivot point times the relationship: $1/[1-\sin(\beta/2)]$, wherein $\beta$ is an angle between planar portions of the part adjacent to the curved portion.

20. The apparatus of claim 17, wherein the linking mechanism includes an upper link and a lower link, each rotatably coupled to the frame, the plunger, and a sensor block such that the relative orientation of the sensor block is maintained when the plunger moves.

21. An apparatus for inspecting a curved portion of a manufactured part, the apparatus comprising:
a plurality of sensing elements that are positioned on a concave arcuate surface, each sensing element configured to transmit and receive a signal;
a plunger configured to contact a surface of the part and move normal to the surface relative to a change of a radius of curvature of the curved portion of the part; and
a linking mechanism coupled to the sensing elements and the plunger and configured to maintain a distance of the sensing elements from a surface of the part in response to relative motion of the plunger, the distance corresponding to a sum of a radius of curvature of the concave arcuate surface and the radius of curvature of the curved portion.

* * * * *